United States Patent
Vallabhaneni

(10) Patent No.: US 11,149,299 B2
(45) Date of Patent: Oct. 19, 2021

(54) METHOD AND SYSTEM FOR MULTIPLEX PROFILING OF CHROMOSOMES IN BIOLOGICAL SAMPLES USING TARGET-SPECIFIC DNA PROBES

(71) Applicant: Ramesh Vallabhaneni, Orlando, FL (US)

(72) Inventor: Ramesh Vallabhaneni, Orlando, FL (US)

(*) Notice: Subject to any disclaimer, the term of this patent is extended or adjusted under 35 U.S.C. 154(b) by 9 days.

(21) Appl. No.: 15/189,120

(22) Filed: Jun. 22, 2016

(65) Prior Publication Data
US 2016/0376639 A1   Dec. 29, 2016

Related U.S. Application Data

(60) Provisional application No. 62/184,347, filed on Jun. 25, 2015, provisional application No. 62/195,564, filed on Jul. 22, 2015.

(51) Int. Cl.
| | | |
|---|---|---|
| *C12Q 1/68* | (2018.01) | |
| *C12Q 1/6818* | (2018.01) | |
| *C12Q 1/6841* | (2018.01) | |

(52) U.S. Cl.
CPC ......... *C12Q 1/6818* (2013.01); *C12Q 1/6841* (2013.01)

(58) Field of Classification Search
USPC .................. 435/6.1, 6.11, 91.1; 436/94, 501; 536/23.1, 24.3
See application file for complete search history.

(56) References Cited

U.S. PATENT DOCUMENTS

| | | | |
|---|---|---|---|
| 5,817,462 A | * | 10/1998 | Garini .................. C12Q 1/6841 506/9 |
| 7,943,304 B2 | | 5/2011 | Vallabhaneni |
| 8,574,836 B2 | | 11/2013 | Vallabhaneni |

OTHER PUBLICATIONS

Gill et al., Fluorescence enhancement at hot-spots: the case of Ag nanoparticle aggregates. Phys. Chem. Chem. Phys., 13, 16366-16372, 2011.*
Fauth et al., Classifying by colors: FISH-based genome analysis. Cytogenet. Cell Gent., 93, 1-10, 2001.*

* cited by examiner

*Primary Examiner* — Frank W Lu
(74) *Attorney, Agent, or Firm* — David Guerra

(57) ABSTRACT

The present invention comprises methods and systems to profile individual chromosomes using target-specific DNA probes in biological samples. The invention relates to generation of chromosome profiles either singly or in combination (multiplex). The invention can refer to the generation of chromosome profiles using target-specific DNA probes for various biological samples such as cell free DNA from the peripheral blood of a pregnant woman or from a cancer patient. The invention further involving generation of chromosome profiles using target-specific DNA probes for individual intact cells from the peripheral blood of a pregnant woman, from a cancer patient or from an embryo created using artificial reproductive technologies. The invention further involving detection of target-specific DNA hybridizations through direct fluorescence by special spectral filters or fluorescence intensity by fluorimeters. Alternatively, chemiluminescent system can be used for detecting target-specific DNA hybridizations indirectly through enzyme-substrate reactions using poly-HRP as enzyme and enhanced luminol as substrate.

12 Claims, 8 Drawing Sheets

METHOD AND SYSTEM FOR MULTIPLEX PROFILING OF CHROMOSOMES IN BIOLOGICAL SAMPLES USING TARGET-SPECIFIC DNA PROBES

CROSS-REFERENCE TO RELATED APPLICATION

This application is a U.S. non-provisional utility application under 35 U.S.C. § 111(a) based upon U.S. provisional applications 62/184,347 filed on Jun. 25, 2015 and 62/195,564 filed on Jul. 22, 2015. Additionally, this U.S. non-provisional utility application claims the benefit of priority of U.S. provisional applications 62/184,347 filed on Jun. 25, 2015 and 62/195,564 filed on Jul. 22, 2015. The entire disclosure of the prior applications is incorporated herein by reference.

BACKGROUND OF THE INVENTION

Field of the Invention

The present invention relates to methods and systems to profile individual chromosomes using target-specific DNA probes in biological samples. Specifically, the methods and systems disclosed herein relate to generation of chromosome profiles either singly or in combination (multiplex). More specifically, the methods and systems disclosed herein refer to the generation of chromosome profiles using target-specific DNA probes for various biological samples such as cell free DNA from the peripheral blood of a pregnant woman or from a cancer patient; the methods and systems further involving generation of chromosome profiles using target-specific DNA probes for individual intact cells from the peripheral blood of a pregnant woman, from a cancer patient or from an embryo created using artificial reproductive technologies such as in vitro fertilization.

Description of the Prior Art

Karyotype identifies the fetal chromosome status from a pregnant woman's diagnostic sample obtained from amniocentesis or chorionic villi. Due to the risks inherent in such invasive procedures, lot of attention has been placed recently on noninvasive screening methods utilizing the cell free fetal DNA in the maternal blood. However, these techniques fail to identify balanced rearrangements in the karyotype. De novo balanced rearrangements are associated with an increased risk for the fetus for various malformations—congenital or at later stage in development. Another type of balanced rearrangement namely Robertsonian translocations which involve acrocentric chromosomes, are associated with increased recurrence risk for trisomy.

Karyotype also plays a major role in the diagnosis and prognosis of many solid malignancies (tumors). However, obtaining successful karyotypes from the solid tumors is often very difficult due to high culture failures. Therefore, similar to the prenatal situation, many efforts have concentrated on the noninvasive techniques. By using cell free circulating tumor DNA, various investigators have developed focused strategies in assessing the specific gene mutation status. However, in practice the primary tumor origin is not known and therefore focused studies produce limited information. This becomes very critical in the early detection of a cancer. Additionally, several tumors have a specific balanced translocation that is diagnostic and can only be detected on intact cells.

In both prenatal and cancer situations, similar attempts to obtain genetic information, are being conducted on circulating intact cells as well. The number of circulating fetal or tumor cells are extremely small and often only one or two from several milliliters of whole blood. Thus obtaining a complete karyotype from profiling all 24 chromosomes from a single cell or few cells will be extremely beneficial.

The existing systems cannot detect the balanced translocations that are diagnostic of all malignancies. They also cannot detect the Robertsonian translocations which are crucial for genetic counselling and risk assessment purposes for pregnant women.

The major drawbacks of the current systems using cell free DNA and intact cells are: 1) longer TAT; 2) higher cost; 3) limited aneuploidy detection; 4) variability of sensitivity among different chromosomal aneuploidy detection; and 5) high infrastructure cost.

The current invention is an improvement over the existing technologies, because it can capture the whole genome information by the use of specially designed fluorescence filter cubes with distinct excitation and emission spectral characteristics of the fluorophores attached to the target-specific DNA probes. Further with the use of "layers" from simple off the shelf programs such as Adobe Photoshop, one can "pull out" the desired target information. Even when several targets are overlapping each other in an interphase cell, by selectively "calling" (looking for) the pre-defined patterns for individual targets, one can trace an entire chromosome in the cell. This will provide the ability to recognize various abnormalities.

The invention solves the problem of the need to do massive parallel sequencing and other tedious testing modalities of the genome to detect fetal aneuploidy from mother's blood and other chromosome changes in cancer patient's peripheral blood by profiling selected targets on individual chromosomes present in the cell free DNA.

Therefore, a need exists for a new and improved method and system for profiling chromosomes singly or in a multiplex mode. In this regard, the present invention substantially fulfills this need. In this respect, the method and system according to the present invention substantially departs from the conventional concepts and designs of the prior art, and in doing so provide an apparatus primarily developed for the purpose of profiling chromosomes for various biological samples using target-specific DNA probes.

SUMMARY OF THE INVENTION

In view of the foregoing disadvantages inherent in the known types of genetic methods to detect various chromosome abnormalities now present in the prior art, the present invention provides an improved method and system to profile chromosomes by using target specific DNA probes for various biological samples, and overcomes the above-mentioned disadvantages and drawbacks of the prior art. As such, the general purpose of the present invention, which will be described subsequently in greater detail, is to provide a new and improved method and system to profile chromosomes by using target specific DNA probes for various biological samples which has all the advantages of the prior art mentioned heretofore and many novel features that result in a method and system to profile chromosomes by using target specific DNA probes which is not anticipated, rendered obvious, suggested, or even implied by the prior art, either alone or in any combination thereof.

To attain this, the present invention essentially comprises, in one aspect, a method for profiling individual chromosomes using cell free DNA from biological samples. The method comprises the steps of:

Collecting and transporting 10-20 ml of peripheral blood using cell free DNA Blood collection tube, for example, using a collection tube provided by Streck Inc.;

Extracting plasma DNA using THP protocol;

Doing overnight Whole genome amplification with blunt ligation of cell free DNA fragments;

Doing 5' end labeling with Biotin;

Ethanol precipitating the DNA fragments;

Incubating Strepavidin Dynabeads beads and biotin-labelled DNA fragments in 96 well plate with or without BHW buffer;

Applying magnet, washing off unbound DNA;

Releasing magnet, doing hybridization with target-specific DNA probes with specific fluorophores for each individual chromosome;

Applying magnet, washing off excess probe with or without BHW buffer;

Eluting with NaOH and with or without buffer from Gills paper;

Applying magnet, transferring elution to fresh 96-well plate;

Adding negatively charged Silver particles and spermine;

Incubating at room temp for 10 minutes in dark;

Taking readings for all fluorophores for each individual chromosome from each well of the 96 well plate using the Fluorimeter;

Establishing the emission curves for each specific target on each chromosome; and Comparing the values with established normal curves for respective targets on all chromosomes.

In another aspect, the method further involves profiling chromosomes on intact cells isolated, recovered or extracted from biological samples. The method comprises the steps of:

Fixing the intact cell(s) on to multi-chambered slides;

Generating target-specific DNA probes;

Doing FISH hybridizations for all targets in one reaction;

Doing FISH hybridizations for targets on six chromosomes at a time;

Repeating hybridizations on intact cells multiple times as needed;

Capturing images of the hybridized targets using specially designed filter cubes;

Analyzing each target and assigning its pre-defined number; and

Completing the chromosome profiling based on the hybridization patterns.

In some embodiments, the fluorescent dye attached to the DNA sequences that makes up the target specific DNA probe, can be Fluorescein 12 dUTP.

In some embodiments, the fluorescent dye attached to the DNA sequences that makes up the target specific DNA probe, can be Cyanin 55345 dUTP.

In some embodiments, the fluorescent dye attached to the DNA sequences that makes up the target specific DNA probe, can be Cyanin 65455 dUTP.

In some embodiments, the fluorescent dye attached to the DNA sequences that makes up the target specific DNA probe, can be 594 dUTP.

In some embodiments, the fluorescent dye attached to the DNA sequences that makes up the target specific DNA probe, can be any fluorophore with excitation and emission characteristics in the range of 200 to 1000 nm.

In some embodiments, the fluorescent dye attached to the DNA sequences that makes up the target specific DNA probe, can be combination of any of the fluorophores with excitation and emission characteristics in the range of 200 to 1000 nm.

In some embodiments, the cell free DNA can be from peripheral blood of a pregnant woman.

In some embodiments, the cell free DNA can be from the peripheral blood of a cancer patient.

In some embodiments, the intact cell(s) can be from the peripheral blood of a cancer patient.

In some embodiments, the intact cell(s) can be from the peripheral blood of a pregnant woman.

In some embodiments, the intact cell(s) can be from the trophectoderm of an embryo formed using artificial reproductive technologies such as in vitro fertilization.

In yet another aspect, a composite karyotype can be generated by pooling all individual chromosome profiles generated from a biological sample.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently described, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved method and system for profiling chromosomes in biological samples using target-specific DNA probes that has all of the advantages of the prior art and none of the disadvantages.

It is another object of the present invention to provide a new and improved method and system for profiling chromosomes in biological samples using target-specific DNA probes that may be easily and efficiently manufactured and marketed.

An even further object of the present invention is to provide a new and improved method and system for profiling chromosomes in biological samples using target-specific DNA probes that has a low cost of manufacture with regard to both materials and labor, and which accordingly is then susceptible of low prices of sale to the consuming public, thereby making such method and system for profiling chromosomes in biological samples using target-specific DNA probes economically available to the buying public.

Still another object of the present invention is to provide a new method and system for profiling chromosomes in biological samples using target-specific DNA probes that provides in the apparatuses and methods of the prior art some of the advantages thereof, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof.

Such description makes reference to the annexed drawings wherein:

FIG. 3 depicts the profile of abnormal chromosome 1 illustrating trisomy.

FIG. 4 depicts the profile of abnormal chromosome 1 illustrating monosomy.

FIG. 5 depicts the profile of abnormal chromosome 1 illustrating an unbalanced translocation with a net duplication of the short arm.

FIG. 6 depicts the profile of abnormal chromosome 1 illustrating deletion of the terminal short arm.

FIG. 7 depicts the profile of abnormal chromosome 1 illustrating deletion of the terminal long arm.

FIG. 8 depicts the profile of abnormal chromosome 1 illustrating an isochromosome for the long arm with a net duplication of the long arm and deletion of the short arm.

DETAILED DESCRIPTION OF THE INVENTION

Figure 1:
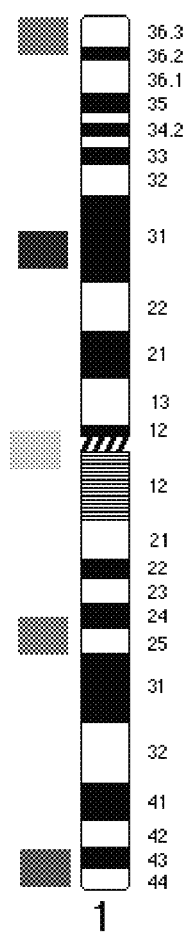
FIG. 1 depicts exemplary embodiments demonstrating that target-specific DNA probes with specific fluorophores DEAC, FITC, Cy3, CY5, Red can be used to generate chromosome profiles.
Figure 2:
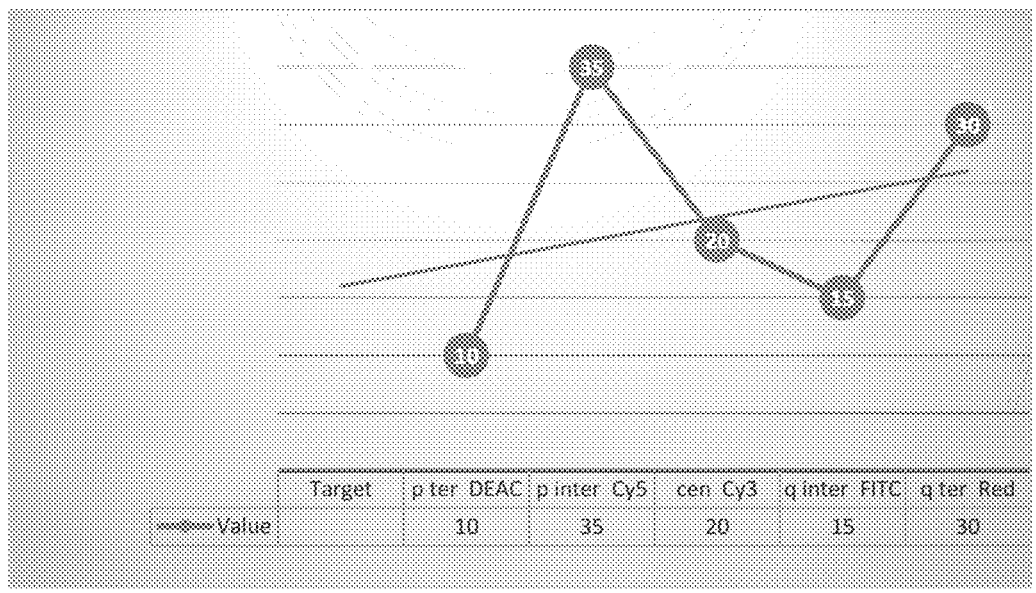
FIG. 2 depicts the profile of a normal chromosome 1 showing all targets with their respective fluorophores and corresponding intensities.
Figure 3:
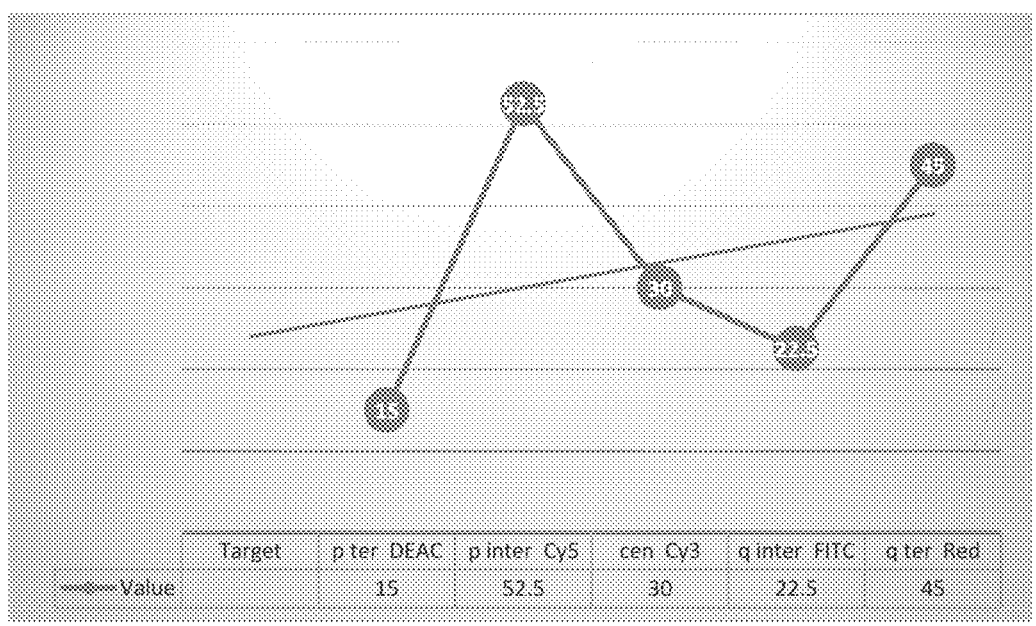
FIGS. 3-8 depict exemplary embodiments demonstrating abnormal profiles of chromosome 1.
Figure 4:
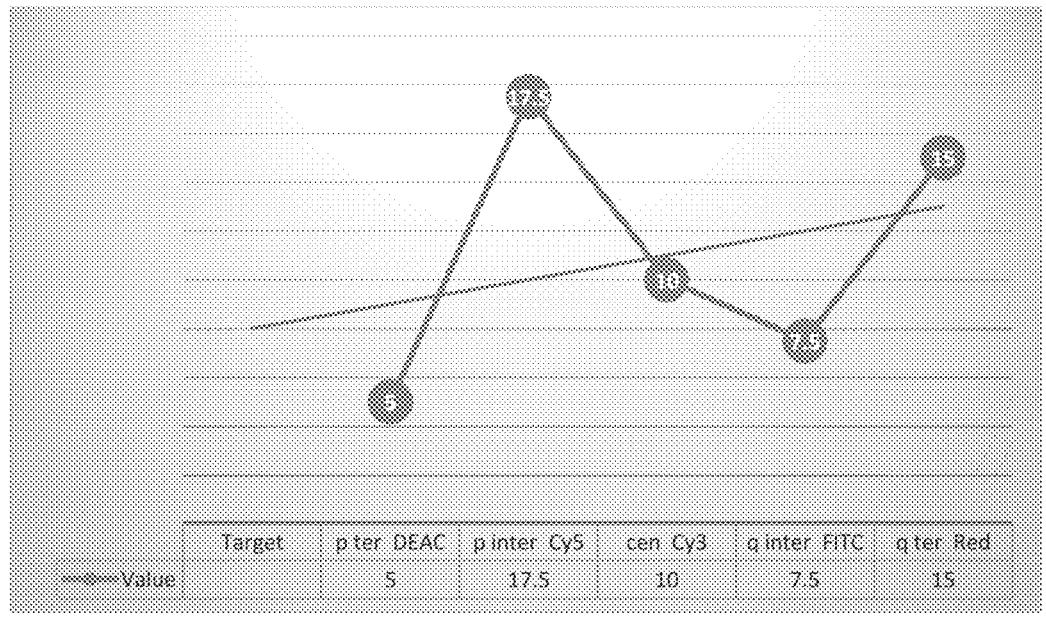
Figure 5:
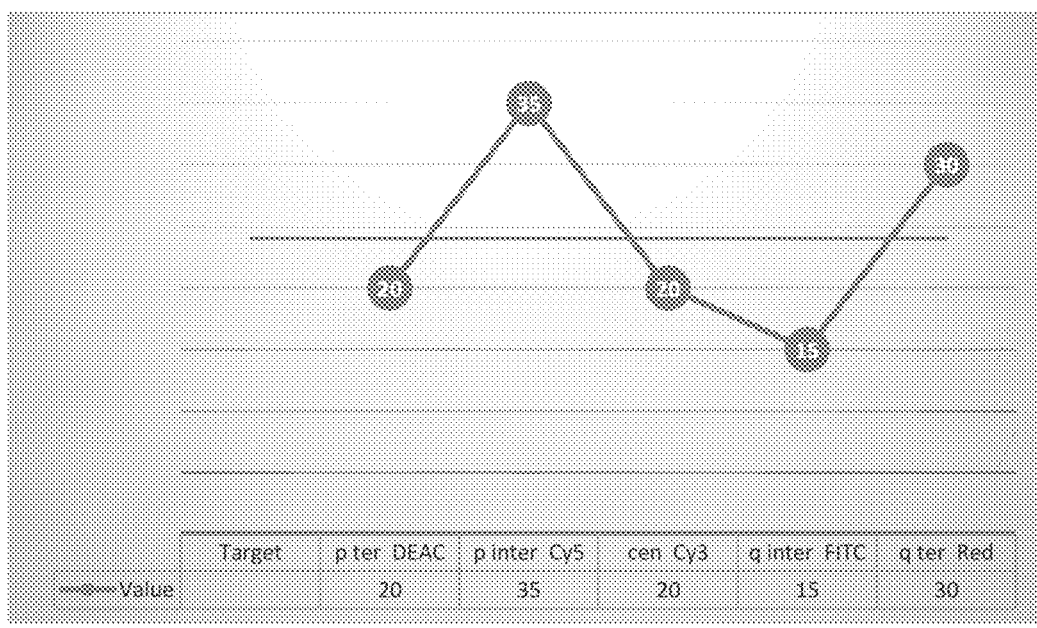
Figure 6:
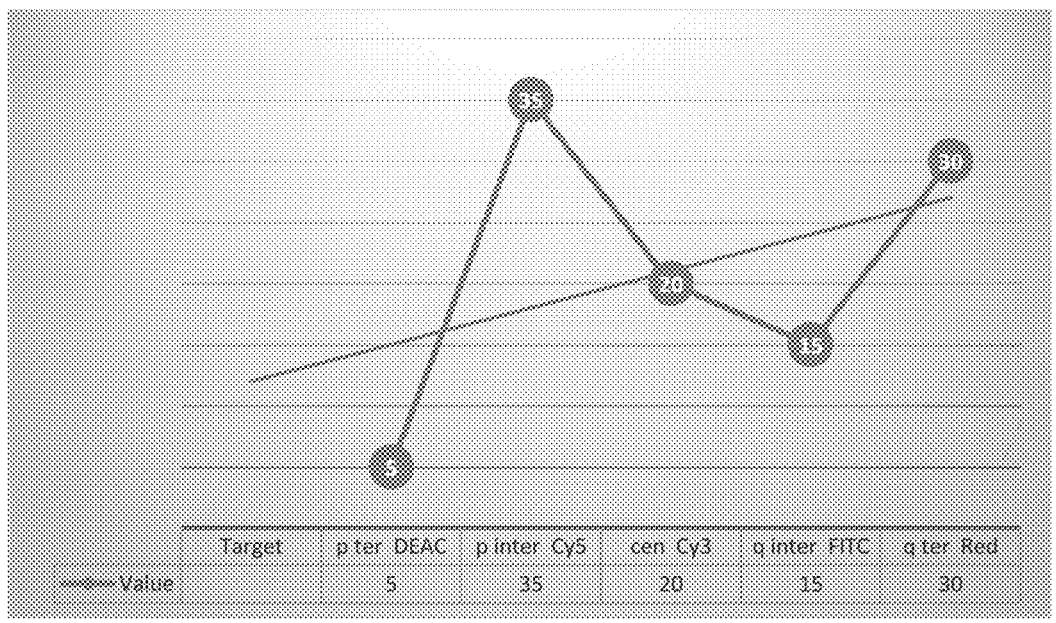
Figure 7:
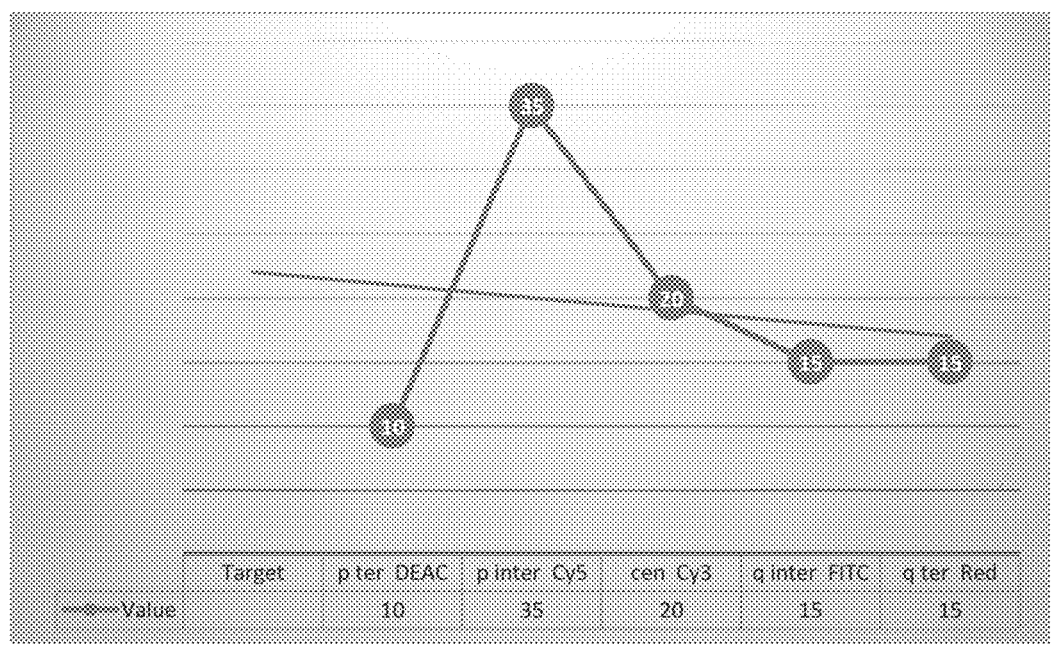
Figure 8:
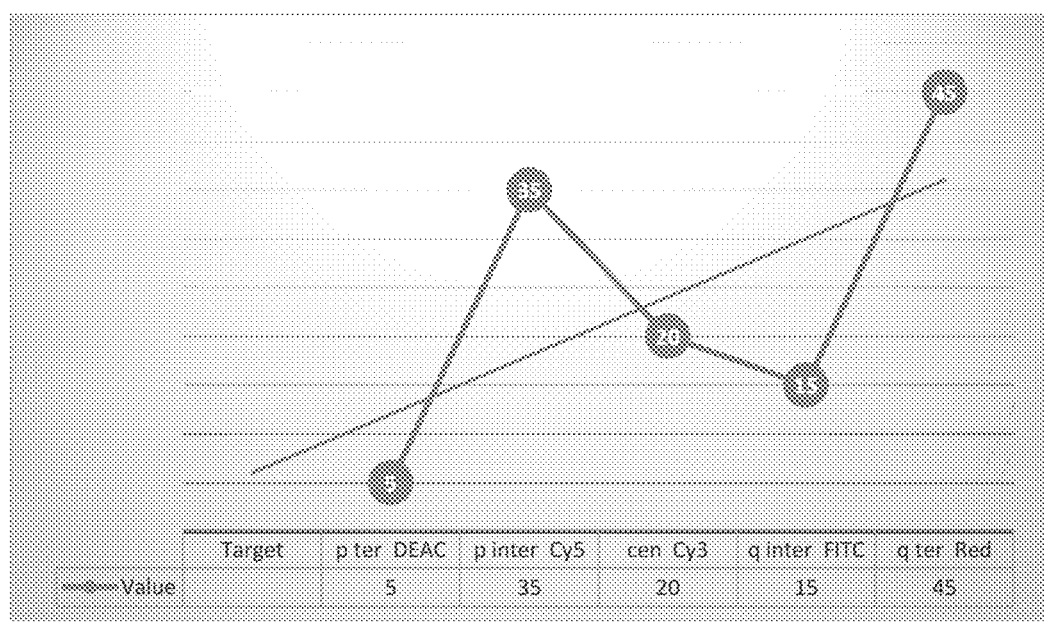
Figure 9:
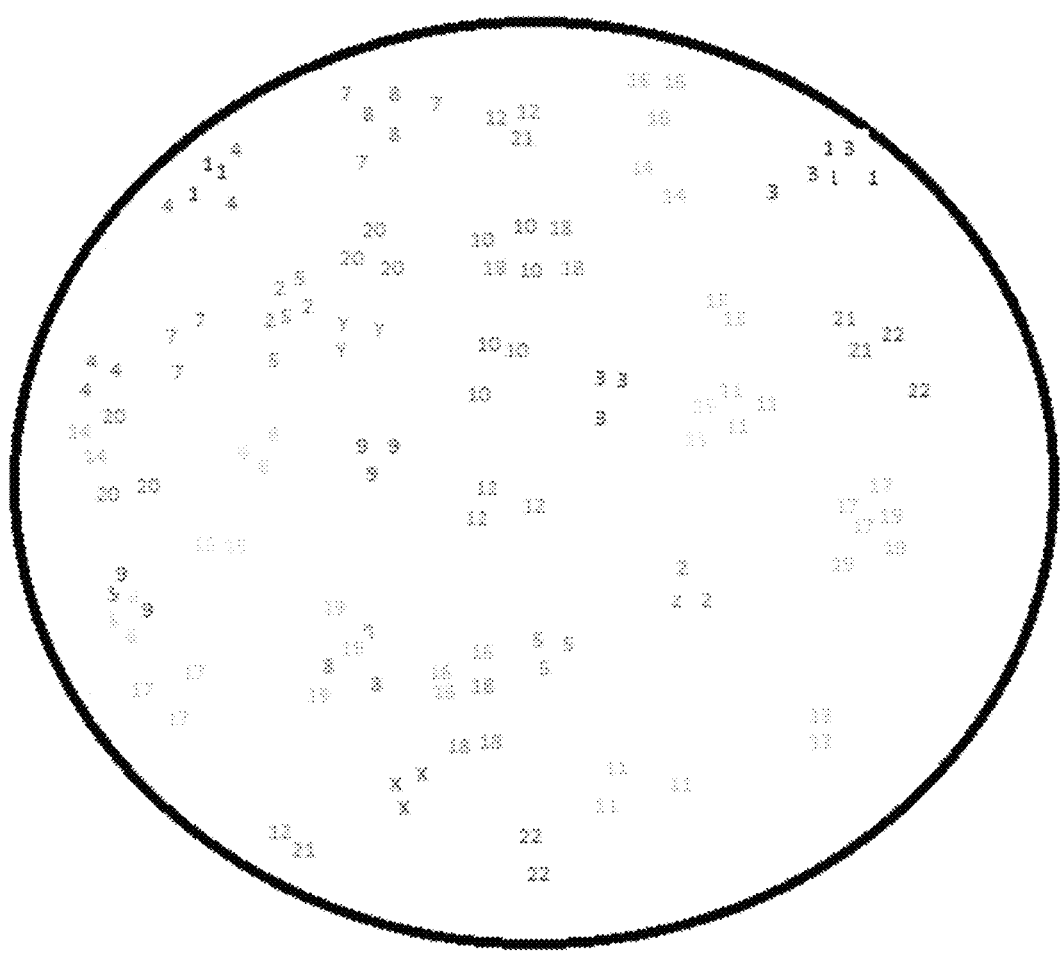
FIG. 9 depicts the target maps based on the in situ hybridization signal patterns of all 70 targets illustrating the profiling of all 24 chromosomes in an intact cell, further demonstrating a translocation.
Figure 10:
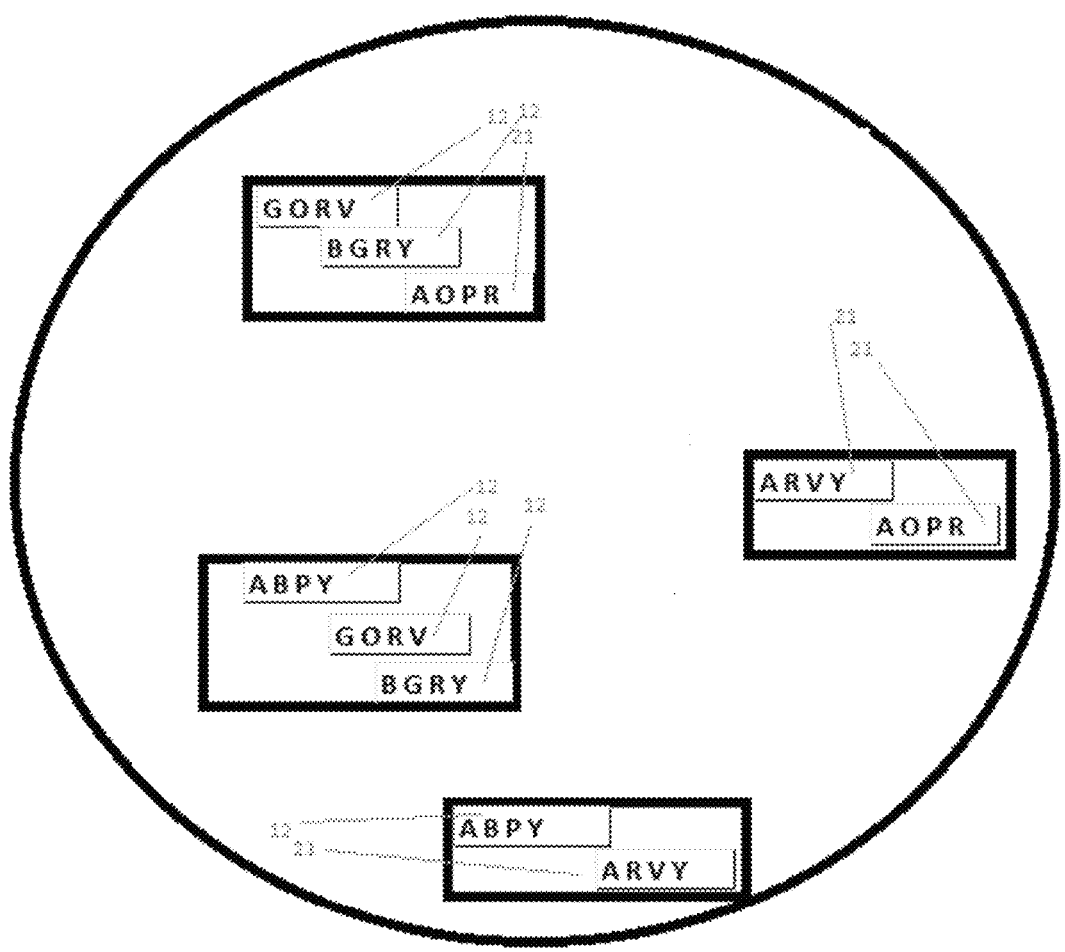
FIG. 10 depicts exemplary embodiments demonstrating that target-specific DNA probes with specific combination of fluorophores can be used to generate chromosome profiles and detect abnormalities as in this case translocation between chromosomes 12 and 21.

Referring now to the drawings, and particularly to FIGS. 1-12, an embodiment of the method and system for profiling chromosomes in biological samples using target-specific DNA probes of the present invention is shown.

As stated above, the claimed invention solves the problem of the need to do massive parallel sequencing of the genome to detect fetal aneuploidy from mother's blood and other chromosome changes in cancer patient's peripheral blood.

The invention utilizes luminescent or fluorescent detection method to detect the amount of DNA present at specific targets along the length of the chromosome by capturing the total amount of fluorescence emitted from the respective fluorophore. The invention utilizes signal enhancing technologies by the use of silver nanoparticles and spermine that will trap the DNA fragments hybridized with specific fluorescent DNA probes. The invention may also utilize signal enhancing technologies by the use of Streptavidin poly-HRP antibodies for binding with biotinylated BAC DNA probes that are designed to target strategic regions of the genome such as telomeres and centromere/pericentromere areas of all chromosomes. The invention also utilizes immobilization technologies to bind amine-modified cell free DNA to specially coated DNA-binding surfaces of the micro titer plates.

The claimed invention differs from what currently exists. Since all existing methods depend on sequencing, all had significant method failures. The current invention is different from the existing sequence-based methods because it employs in situ hybridization platform and signal amplification techniques in both generating the signal and enhancing for fluorescence detection. It is an improvement over the existing methodologies and has the following advantages: 1) fast TAT; 2) lower cost; 3) ease of use in almost all laboratory setups without significant infrastructure expenditure; and 4) comprehensive screening for aneuploidy of all chromosomes.

As stated above, Karyotype identifies the fetal chromosome status from a pregnant woman's diagnostic sample obtained from amniocentesis or chorionic villi. Due to the risks inherent in such invasive procedures, lot of attention has been placed recently on noninvasive screening methods utilizing the cell free fetal DNA in the maternal blood. However, these techniques fail to identify balanced rearrangements in the karyotype. De novo balanced rearrangements are associated with an increased risk for the fetus for various malformations—congenital or at later stage in development. Another type of balanced rearrangement namely Robertsonian translocations which involve acrocentric chromosomes, are associated with increased recurrence risk for trisomy.

Karyotype also plays a major role in the diagnosis and prognosis of many solid malignancies (tumors). However, obtaining successful karyotypes from the solid tumors is often very difficult due to high culture failures. Therefore, similar to the prenatal situation, many efforts have concentrated on the noninvasive techniques. By using cell free circulating tumor DNA, various investigators have developed focused strategies in assessing the specific gene mutation status. However, in practice the primary tumor origin is not known and therefore focused studies produce limited information. This becomes very critical in the early detection of a cancer. Additionally, several tumors have a specific balanced translocation that is diagnostic and can only be detected on intact cells.

In both prenatal and cancer situations, similar attempts to obtain genetic information, are being conducted on circulating intact cells as well. The number of circulating fetal or tumor cells are extremely small and often only one or two from several milliliters of whole blood. Thus obtaining a complete karyotype from a single or few cells will be extremely beneficial. The invention claimed here solves this problem.

The claimed invention solves the above mentioned problems by utilizing a comprehensive approach of probing the whole genome. By targeting specific landmarks on chromosomes such as telomeres and centromeres, and making them molecularly distinct (unique), the invention can identify all balanced translocations as well as unbalanced changes from a single or few cells obtained from peripheral blood of a pregnant woman, or cancer patient or from an embryo.

The claimed invention is an improvement and differs from what currently exists. It utilizes the fluorescence in situ hybridization (FISH) technology and it is better since all targets on all chromosomes are designed to be molecularly distinct, whole genome can be interrogated for abnormalities, balanced as well as unbalanced, from a single or few cells. This invention detects even the special type of rearrangement i.e., Robertsonian translocation, by recognizing the juxta-positioned centromere landmarks of the two involved acrocentric chromosomes. For example, this reveals the mechanism of Down syndrome—free standing trisomy vs. translocation related trisomy. Since existing systems concentrate on disease-specific detection, they don't work well for the whole genome investigations. When the available material is so restricted such as a single or few cells, even whole genome amplification after the DNA extraction cannot provide comprehensive detection capabilities.

The current invention is an improvement over the existing technologies, because with the use of specially designed BAC DNA probes, it can capture the whole genome (karyotype) information by the use of specially designed fluorescence filter cubes with distinct excitation and emission spectral characteristics. Further with the use of "layers" from simple off the shelf programs such as Adobe Photoshop, one can "pull out" the desired target information. Even when several targets are overlapping each other in an interphase cell, by selectively "calling" (looking for) the pre-defined patterns for individual targets, one can trace an entire chromosome in the cell. This will provide the ability to recognize various abnormalities.

Embodiments of the present invention may include, but not limited to:
1) Obtaining peripheral blood and separating plasma; if needed using stabilizers for transporting the collected blood to the testing facility;
2) Purifying the cell free (cf) DNA using either commercial kits like Qiagen amp kits or in house protocols like Triton/Heat/Phenol (THP) Protocol;
3) Doing Whole Genome Amplification (WGA) using blunt ligated method with (BLM-PCR) or without (BL-WGA) enriching the fragment size;
4) Doing 5' end labeling with Biotin;
5) Ethanol precipitating the DNA fragments;
6) Incubating Strepavidin Dynabeads beads and biotin-labelled DNA fragments in 96 well plate with or without BHW buffer;
7) Applying magnet, washing off unbound DNA;
8) Releasing magnet, doing hybridization with target-specific DNA probes with specific fluorophores for each individual chromosome;
9) Applying magnet, washing off excess probe with or without BHW buffer;
10) Eluting with NaOH and with or without buffer from Gills paper;
11) Applying magnet, transferring elution to fresh 96-well plate;
12) Adding negatively charged Silver particles and spermine;
13) Incubating at room temp for 10 minutes in dark;
14) Detecting the fluorescence with fluorimeter and comparing with the established standard curves for each target on each chromosome; and
15) Completing the chromosome profiling based on the hybridization patterns.

Additional embodiments of the present invention may include, but not limited to:
16) Labeling DNA probes with biotin;
17) Generating the signal through indirect enzymatic methods such as avidin-poly HRP complex;
18) Using enhanced Luminol as a substrate for the poly HRP enzyme; and
19) Detecting the signal using Luminometer.

Yet additional Embodiments of the present invention may include, but not limited to:
20) Isolating the circulating fetal or tumor cell(s) from peripheral blood or trophoblast cells from embryo;
21) Fixing the intact cell(s) on to multi-chambered slides;
22) Generating target-specific DNA probes;
23) Doing FISH hybridizations for all targets in one reaction;
24) Doing FISH hybridizations for targets on six chromosomes at a time;
25) Repeating hybridizations on intact cells multiple times as needed;
26) Capturing images of the hybridized targets using specially designed filter cubes;
27) Analyzing each target's hybridization patterns; and
28) Completing the chromosome profiling based on the hybridization patterns.

It can be appreciated that drawings may include alternate depictions of probe labelling and signal detection such as but not limited to:

FIG. 1 can also depict exemplary embodiments demonstrating that target-specific DNA probes with fluorophores orange, Cy3.5, Cy5.5, Cy7, Cy7.5 can be used to generate chromosome profiles.

FIGS. 3-8 can also depict exemplary embodiments demonstrating abnormal profiles of any of the 24 chromosomes illustrating any abnormality.

Figure 11:
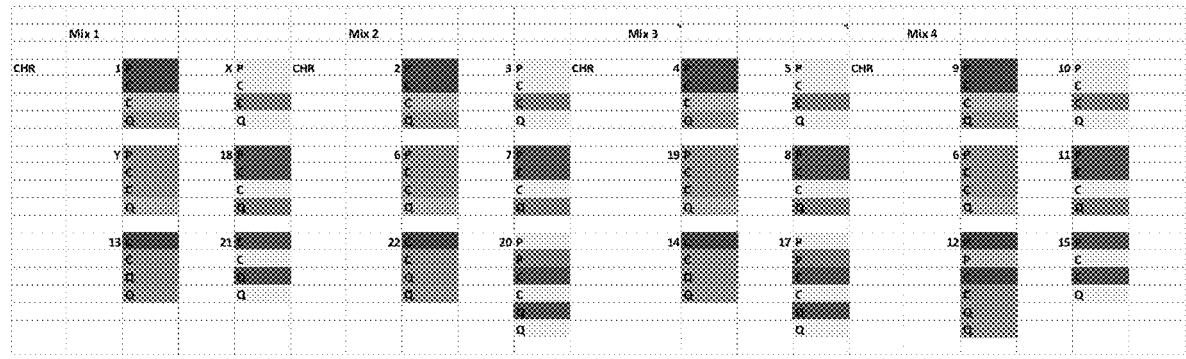
FIG. 11 depicts the fluorophore color scheme a) Multiplex Profiling of chromosomes 1, Y, 13 using target-specific DNA probes b) Multiplex Profiling of chromosomes X, 18, 21 using target-specific DNA probes c) Multiplex Profiling of chromosomes 2, 6, 22 using target-specific DNA probes d) Multiplex Profiling of chromosomes 3, 7, 20 using target-specific DNA probes e) Multiplex Profiling of chromosomes 4, 19, 14 using target-specific DNA probes f) Multiplex Profiling of chromosomes 5, 8, 17 using target-specific DNA probes g) Multiplex Profiling of chromosomes 9, 16, 12 using target-specific DNA probes h) Multiplex Profiling of chromosomes 10, 11, 15 using target-specific DNA probes.

FIG. 11 can also depict the fluorophore color scheme of multiplex profiling of any combination of three of the 24 human chromosomes.

Figure 12A:
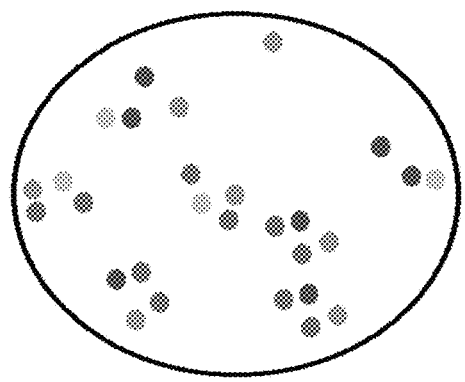
FIG. 12A depicts multiplex profiling of chromosomes 1, Y, 13 illustrating trisomy 13 and balanced translocation involving the long arm of chromosome 1.
Figure 12B:
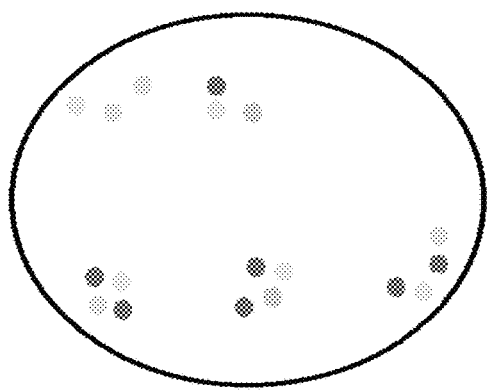
FIG. 12B depicts multiplex profiling of chromosomes X, 18, 21 illustrating monosomy X and deletion of the short arm of chromosome 18.

FIG. 12 can also depict multiplex profiling of any combination of chromosomes illustrating any type of abnormalities.

For detecting genetic abnormalities through chromosome profiling in a noninvasive way, first the plasma is separated from the whole blood and in the next step, the cell free DNA is extracted. The purified DNA is amplified in step 3. Step 4 is an integral part of step three, where the genomic DNA fragments are end labelled with Biotin. Step 4 is a pre-requisite for step 5 where the DNA is ethanol precipitated. In Step 6, Strepavidin beads and biotin-labelled genomic DNA fragments are incubated in 96 well plates with appropriate buffer. In the next step, unbound DNA is washed off after the magnetic separation of the beads. This is a pre-requisite for FISH hybridization which is carried out in step 8. After removal of the beads from magnetic field, target-specific DNA probes labelled with specific fluorophore combinations are hybridized to the genomic fragments bound to avidin molecules on the magnetic beads through the avidin-biotin complexes formed in step 6. After releasing the beads from magnetic field, excess DNA probe is washed off and the hybridized probe is eluted with NaOH in appropriate buffer. Individual elusions are transferred to fresh 96 well plate, after magnetic separation of beads. In step 12, fluorescent probes are trapped between the negatively charged silver nanoparticles and positively charged spermin which helps to form silver aggregates. This facilitates the fluorescence signal amplification after a 10 minute incubation at room temperature in dark. In the next step individual fluorescence readings are automatically registered by the fluorimeter. Finally, these readings which will become part of chromosome profiles will be compared against the standard normal chromosome profiles to determine the genetic abnormalities.

For detecting genetic abnormalities through chromosome profiling in a noninvasive way, in addition to using plasma DNA, intact cells are also used. Isolating the circulating fetal or tumor cell (s) from peripheral blood or trophoblast cells from embryo is a pre-requisite for the next step where the isolated cells will be fixed onto the microscope slides. The target-specific BAC probes generated in the next step will be used for FISH hybridization in the following steps either targeting all chromosomes in one reaction or six chromosomes at a time. In the following step, repeat hybridizations are performed as many times as needed to complete hybridizations of all genomic targets. In the next step, images of hybridized targets will be captured, which are used for analysis in the next step. In the last step, using the predefined criteria the observed targets will be determined to constitute a normal or abnormal condition.

The following is exemplary of how an embodiment of the present invention can work.

Preservation of cell free DNA in the plasma can be accomplished by using well established preservatives and the sample can be shipped to laboratories around the world without degradation of the cell free DNA. Multiple methodologies exist to extract and purify the high molecular weight DNA. By optimally procuring the sample and preparing the cell free DNA, one can utilize any one of many whole genome amplification techniques to generate enough quantity to assess the aneuploidy and other abnormalities of all chromosomes. In other words, one can generate a molecular karyotype using the cell free DNA. To accomplish this, one should modify the DNA after amplification step with 5'end-labeling with biotin. Several methods exist to trap these DNA fragments onto solid surfaces. The most efficient way would be to incubate the Streptavidin magnetic beads with the biotinylated DNA fragments. Generation of target-specific DNA probes with specific fluorophores can be achieved by the standard nick translation protocols. Once desired probes are generated, individual chromosome FISH reactions can be carried out on the beads in micro titer plates in appropriate hybridization buffers. The hybridized probes can be eluted and transferred to fresh microtiter plate. Multiple amplification technologies are available for enhancing fluorescence. One such method is the use of silver nanoparticles in combination with spermine. Specific fluorescence intensities can be recorded from each well (chromosome). The principal application of this novel approach will be to detect increased or decreased levels of genomic targets in reference to established curves for a cell free DNA quantity in a normal female or non-cancer control individuals. By combination of the above mentioned steps, one can screen for chromosomal aneuploidy and other changes such as deletions and duplications. In other words, a molecular karyotype can be generated with this novel method using cell free DNA from maternal blood and blood from all cancer patients. Therefore, chromosome changes related to solid cancers can also be detected using cell free DNA from the peripheral blood of cancer patients using the above method.

Several methods exist to separate and enrich either fetal or tumor cells from the peripheral blood. By optimally procuring the desired cells, one can fix them to the surface of the microscope slide. Generation of target-specific DNA probes with the preset color combinations (FIG. 11) can be achieved by the standard nick translation protocols. Once desired probes are generated, hybridization for all genome targets can be carried rapidly on the microscope slide. By repeating the hybridizations as needed, all 24 chromosomes can be profiled in less than 24 hours.

With the use of specially designed fluorescence filter sets and camera, one can capture the images. This data set will serve as the basis for analysis of the individual targets using layers in Photoshop. Determination of individual chromosome status is possible by the combination of these above mentioned steps. Once individual chromosomes are identified, generating a full karyotype is a standard procedure for those skilled in the art.

The following is exemplary of how a person skilled in the art can use an embodiment of the present invention.

Several centrifugation methods are available to separate the plasma component from the whole blood collected from a pregnant mother. Similarly, multiple DNA extraction and purification technologies exist for those skilled in the art to utilize. Commercially available kits can be used for this step or home-brew methods such as THP protocol are very useful. Several whole genome amplification kits are commercially available. Of these, the blunt ligated amplification method with or without enrichment for fragment size is optimally suited for the investigation of fetal aneuploidy.

For end labeling with biotin, several kits are commercially available. Streptavidin magnetic beads are available readily from multiples vendors.

Specific BAC libraries and fluorophores to generate target-specific DNA probes are commercially available. Silver nanoparticles and spermine are readily available commercially.

Several Fluorimeters are commercially available for use with this novel method.

Several strategies exist in the literature for isolating fetal cells. Of these, separation and enrichment of nucleated fetal red cells offers several advantageous. A simple procedure would be to use magnetic beads coated with monoclonal antibodies against CD71/Glycophorin A. Using a magnetic field, these cells can be separated and enriched. Of many systems for isolation of tumor cells, the filter system by ScreenCell is the simplest and most economical. This system can also be used to separate the fetal cells. They can then be used for FISH on the microscope slides with the target-specific DNA probes generated using standard Nick translation and the scheme outlined in FIG. 11. The fluorescent labels needed to make these probes for each target, are commercially available. In total, four spectrally distinct fluorophores are used with combinations as illustrated (FIG. 11). Fluorescence microscope systems are commercially available for use with the current invention. Of the several commercial sources for excitation/emission filter sets, Semrock and Chroma offer optimal filter combinations to detect all colors. Images can be captured either using a single filter set or a combination of filter sets. This whole process can also be automated using commercially available systems. The default approach is always manual, since this is the most affordable way for many laboratories around the world. Once proper images are captured, they can be uploaded to Photoshop for further analysis. Commercial software programs are available for this type of analysis; however as with the previous step, use of the off shelf programs such as Adobe Photoshop is very economical. One can then analyze each molecularly distinct targets on individual chromosomes using manual or automated protocols to generate chromosome profiles.

In order to screen for fetal aneuploidy from the mother's blood, one with skill in the art would perform the following tasks:

Separate the plasma from the peripheral blood;
Extract and purify cell free DNA;
Ligate the small pieces of cell free DNA and perform whole genome amplification using random hexaprimers;
End label the fragments with Biotin;
Incubate with Streptavidin magnetic beads;
Generate target-specific DNA probes with specific fluorophores;
Perform FISH in 96-well plates;
Incubate with silver nanoparticles and spermin; and
Record the respective fluorescence intensities using fluorimeter.

By comparing with the standard curves established for each fluorophore associated with target-specific DNA probes, one would determine if there is fetal aneuploidy for various chromosomes. Additionally, large deletions and duplications both terminal and interstitial, can be detected using this enhanced fluorescent method (FIGS. 2-8).

For detecting chromosome abnormalities from the primary solid tumors, one would use cell free DNA from peripheral blood and compare the results from cancer patients with the established normal curves.

Even low fraction fetal DNA samples can also be processed with this method. Even though the fetal portion of the cell free DNA is a constant proportion among the total cell free DNA i.e., about 20%, and the difference of one copy of the chromosome which is about 10%, the absolute amount of fluorescence emitted in this system is substantially higher than the 10% difference because of the silver nanoparticle-spermin complexes. Thus the sensitivity of this assay is significantly better than the massive parallel sequencing methods employed currently. Also, it can create: 1) A faster method for detection of fetal aneuploidy from maternal blood; and 2) A more practical approach that can be employed in almost all laboratories unlike the existing methodology offered by only few commercial entities.

Same principles also apply for cancer detection.

In order to determine a full karyotype especially to identify a balanced translocation, from a single intact circulating fetal cell, tumor cell, or trophoblast cell, one with skill in the art would perform the following tasks:

1. Isolate/extract the circulating fetal or tumor cell(s) or trophoblast cells;
2. Fix the cell(s) onto the microscope slide;
3. Generate target-specific DNA probes as per the scheme in FIG. 11 and Table 1;
4. Do FISH hybridizations;
  a) All chromosomes in one hybridization; OR
  b) Six chromosomes at a time as per the modified scheme;
5. Capture images of the hybridized targets using specially designed filter cubes;
6. Analyze each target and assign its pre-defined position as per scheme in FIG. 11; and
7. Identify the chromosome abnormalities and define the karyotype.

TABLE 1

Probe Color combinations for targets on each chromosome

| Ch. No | Code | pter | cen | qter |
|---|---|---|---|---|
| 1 | 1, 70, 36 | ABGV | OPRY | BGVY |
| 2 | 02, 69, 37 | ABVY | GOPR | BGOV |
| 3 | 03, 68, 38 | ABOV | GPRY | BGRV |
| 4 | 04, 67, 39 | ABRV | GOPY | BGPV |
| 5 | 05, 66, 40 | ABPV | GORY | BOVY |
| 6 | 06, 65, 41 | ABGY | OPRV | BRVY |
| 7 | 07, 64, 42 | ABGO | PRVY | BPVY |
| 8 | 08, 63, 43 | ABGR | OPVY | BOVY |
| 9 | 09, 62, 44 | ABGP | ORVY | BOPV |
| 10 | 10, 61, 45 | ABOY | GPRV | BPRV |
| 11 | 11, 60, 46 | ABRY | GOPV | BGOY |
| 12 | 12, 59, 47 | ABPY | GORV | BGRY |
| 13 | 13, 58 | | ABOR | GPVY |
| 14 | 14, 57 | | ABOP | GRVY |
| 15 | 15, 56 | | ABPR | GOVY |
| 16 | 16, 55, 28 | AGVY | BOPR | AGPY |
| 17 | 17, 54, 29 | AGOV | BYPR | AGOR |
| 18 | 18, 53, 30 | AGRV | BOPY | AGOP |
| 19 | 19, 52, 31 | AGPV | BORY | AGPR |
| 20 | 20, 51, 50 | AOVY | BGPR | BGOP |
| 21 | 21, 35 | | ARVY | AOPR |
| 22 | 22, 34 | | APVY | AYPR |
| X | 23, 49, 33 | AORV | BGOR | AOPY |
| Y | 24, 48, 32 | AOPV | BGPY | AORY |

A = Aqua
B = Blue
G = Green
O = orange
P = Purple
R = Red
V = Violet
Y = Yellow
cen = centromere
ter = telomere If additional cells are available, clonality can be established for the abnormality. Further, clonal evolution and tumor heterogeneity can also be studied. If no additional cells are available, one can use other DNA-based methods such as PCR on the cell free circulating DNA from the same patient's plasma sample to confirm the translocation.

For detecting the special balanced translocation involving the five acrocentric chromosomes, namely Robertsonian translocation, one would look for the juxtaposition of any two of the five centromere targets, if they used the methods outlined in step 3 above. If needed, a repeat hybridization can be done utilizing commercially available probe set from InteGen LLC for detecting Robertsonian translocations.

Another application will be use of target-specific DNA probes for determining the telomere length and associations in cancer cells in comparison to normal cells using the repeat hybridization approach mentioned above.

EXAMPLES

Example 1

Establishing Fetal Karyotype from Mother's Blood Through Chromosome Profiling Using Target-Specific DNA Probes on Cell Free Plasma DNA In one embodiment, a fetal karyotype can be established by studying the cell free DNA fragments which are extracted from pregnant mother's plasma, amplified and labelled with biotin. The fragments can be bound to magnetic streptavidin beads through the conjugation of avidin-biotin complexes. The DNA fragments can be hybridized to their complimentary sequences through target-specific fluorophore labelled DNA probes. The hybridized probes can be eluted and sandwiched between shiver nanoparticles and spermine complexes to enhance their fluorescence.

The intensity of each fluorophore can be recorded by a fluorimeter and individual intensity curves reflecting the DNA amount can be generated. These curves can be compared with the established normal curves to determine the presence and type of any abnormality. By following the above steps, individual chromosome profiles can be generated and by combining all 24 chromosome profiles, a fetal karyotype can be established.

Example 2

Establishing Solid Tumor Diagnosis from Patients' Blood Through Chromosome Profiling Using Target-Specific DNA Probes on Cell Free Plasma DNA In another embodiment, a tumor karyotype can be established by studying the cell free DNA fragments which are extracted from cancer patient's plasma, amplified and labelled with biotin. The fragments can be bound to magnetic streptavidin beads through the conjugation of avidin-biotin complexes. The DNA fragments can be hybridized to their complimentary sequences through target-specific fluorophore labelled DNA probes. The hybridized probes can be eluted and sandwiched between shiver nanoparticles and spermine complexes to enhance their fluorescence. The intensity of each fluorophore can be recorded by a fluorimeter and individual intensity curves reflecting the DNA amount can be generated. These curves can be compared with the established normal curves to determine the presence and type of any abnormality. By following the above steps, individual chromosome profiles can be generated and by combining all 24 chromosome profiles, a karyotype can be established. Based on the result of that karyotype, specific tumor diagnosis can be established.

Example 3

Establishing Fetal Karyotype from Mother's Blood Through Chromosome Profiling Using Target-Specific DNA Probes on Intact Circulating Fetal Cells In another embodiment, a fetal karyotype can be established by hybridizing target-specific DNA probes to intact circulating fetal cells. Fetal cells can be isolated from mother's blood through various established techniques. DNA hybridizations can be done for all chromosome targets in one reaction or targets from six chromosomes can be assessed in each reaction. This can be followed by the required number of repeat hybridizations on the intact cell(s) to complete the profiling. Individual chromosome hybridization patterns can be recorded and compared to the expected normal patterns to determine the presence and type of any abnormality. By following the above steps, a fetal karyotype can be established.

Example 4

Establishing Solid Tumor Diagnosis from Patients' Blood Through Chromosome Profiling Using Target-Specific DNA Probes on Intact Circulating Tumor Cells In another embodiment, a specific tumor diagnosis can be established by hybridizing target-specific DNA probes to intact circulating tumor cells. Tumor cells can be isolated from patient's blood through various established techniques. DNA hybridizations can be done for all chromosome targets in one reaction or targets from six chromosomes can be assessed in each reaction. This can be followed by the required number of repeat hybridizations on the intact cell(s) to complete the profiling. Individual chromosome hybridization patterns can be recorded and compared to the expected normal patterns to determine the presence and type of any abnormality. By following the above steps, a specific tumor diagnosis can be established.

Example 5

Establishing an Embryo Karyotype Through Chromosome Profiling Using Target-Specific DNA Probes on Intact Cells from Trophectoderm Layer In another embodiment, an embryo karyotype can be established by hybridizing target-specific DNA probes to intact fetal cells. Fetal cells can be isolated from trophectoderm layer of an embryo through various established techniques. DNA hybridizations can be done for all chromosome targets in one reaction or targets from six chromosomes can be assessed in each reaction. This can be followed by the required number of repeat hybridizations on the intact cell(s) to complete the profiling. Individual chromosome hybridization patterns can be recorded and compared to the expected normal patterns to determine the presence and type of any abnormality. By following the above steps, a karyotype can be established for any embryo considered for in vitro fertilization.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in the embodiments of the present invention. Still further variations and alternate elements will be apparent to those skilled in the art. Among these variations without limitation, are the specific number and/or type of fluorophores in a target-specific DNA probe to profile individual chromosomes. Various embodiments of the invention can include or exclude any of these variations or elements.

Furthermore, numerous references have been made to patents and printed publications throughout this specification. Each of the above cited references are herein individually incorporated by reference in their entirety.

Finally, it is to be understood that the embodiments of the invention disclosed herein are illustrative of the principles of the present invention. Other modifications that can be employed can be within the scope of the invention. Therefore, by way of example, but not of limitation, alternative configurations of the present invention can be utilized in accordance with the teachings herein. Accordingly, embodiments of the present invention are not limited to that precisely as shown and described.

While embodiments of the method and system for profiling chromosomes in biological samples by using target specific DNA probes have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method for multiplex profiling of chromosomes in an intact interphase cell from human biological samples using chromosome-specific DNA probes, said method comprising the steps of:
   a) generating a plurality of specific biotinylated fluorescent DNA probes by attaching one to four different fluorescent labels by nick translation and Biotin by 5' end-labeling to each of said DNA probes such that each of said specific biotinylated fluorescent DNA probes has preset different color combinations and each of said specific biotinylated fluorescent DNA probes emits one to four different fluorescent signals when each of said fluorescent DNA probes is excited;
   b) adding magnetic streptavidin beads to said specific biotinylated fluorescent DNA probes such that at least a portion of said specific biotinylated fluorescent DNA probes binds to said magnetic streptavidin beads in a mixture;
   c) obtaining specific biotinylated fluorescent DNA probes bound with said beads by applying a magnetic field to said mixture and washing off said specific biotinylated fluorescent DNA probes not bound with said beads;
   d) removing away said magnet field after said washing off said fluorescent DNA probes not bound with said beads;
   e) performing hybridization of said specific biotinylated fluorescent DNA probes bound with said beads to specific target DNA sequences on human chromosomes in an intact interphase cell from human biological samples; and
   f) generating the multiplex profiling of chromosomes in the intact interphase cell from the human biological samples including an individual profile for each of said chromosomes by reading, using one or more filter sets, said one to four different fluorescent signals emitted at said specific target DNA sequences on said human chromosomes in said intact interphase cell; wherein said one to four different fluorescent labels is selected from eight different color dyes.

2. The method of claim 1, wherein said hybridization is in situ hybridization.

3. The method of claim 2, wherein said in situ hybridization is done once or multiple times on the said intact interphase cell.

4. The method of claim 2, wherein said in situ hybridization is aimed at said specific DNA sequences on said human chromosomes in a single hybridization.

5. The method of claim 1 further comprising the step of registering individual locations of said one to four different fluorescent signals emitted at said specific DNA sequences on said human chromosomes within said intact interphase cell using specific excitation/emission filter cubes embedded in a fluorescent microscope and a CCD camera.

6. The method of claim 1, wherein said fluorescent labels attached to said specific biotinylated DNA probes are present in a nucleotide used in the nick translation selected from the group consisting of DEAC dUTP, FITC dUTP, Cyanine 3-dUTP, Cyanine 5-dUTP, Red 594 dUTP, and analogs or derivatives thereof.

7. The method of claim 1, wherein said DNA probes are selected from the group consisting of human chromosomes 1-22, X, and Y.

8. The method of claim 1, wherein said individual profile for each of said chromosomes is used to detect a chromosome abnormality selected from the group consisting of a numerical chromosome abnormality, and a structural chromosome abnormality.

9. The method of claim 1, wherein at least one of said human biological samples is selected from the group consisting of peripheral blood from a pregnant woman, peripheral blood from a cancer patient and trophoblast cells from an embryo created using artificial reproductive technologies.

10. The method of claim 1 further comprises, prior to step f), the step of adding negatively charged silver particles and positively charged spermine particles to said specific biotinylated fluorescent DNA probes on said specific target DNA sequences on said human chromosomes in said intact interphase cell to trap said specific target DNA sequences on said human chromosomes hybridized with said specific biotinylated fluorescent DNA probes and enhance fluorescence of said specific biotinylated fluorescent DNA probes.

11. The method of claim 1 further comprises the step of establishing intensity curves for each of said human chromosomes by recording the fluorescent intensity of each of said human chromosomes using a fluorimeter, and comparing the intensity curves for each of said human chromosomes with normal intensity curves of each of normal human chromosomes in a control cell produced using the same method for establishing the intensity curves for each of said human chromosomes.

12. A method for multiplex profiling of chromosomes in an intact interphase cell from human biological samples using chromosome-specific DNA probes, said method comprising the steps of:
   a) generating a plurality of specific biotinylated fluorescent DNA probes by attaching one to four different fluorescent labels by nick translation and Biotin by 5' end-labeling to each of said DNA probes such that each of said specific biotinylated fluorescent DNA probes has preset different color combinations and each of said specific biotinylated fluorescent DNA probes is capable of emitting one to four different fluorescent signals;

b) adding magnetic streptavidin beads to said specific biotinylated fluorescent DNA probes such that at least a portion of said specific biotinylated fluorescent DNA probes binds to said magnetic streptavidin beads in a mixture;

c) obtaining specific biotinylated fluorescent DNA probes bound with said beads by applying a magnetic field to said mixture and washing off said specific biotinylated fluorescent DNA probes not bound with said beads;

d) removing away said magnet field after said washing off said fluorescent DNA probes not bound with said beads;

e) performing hybridization of said specific biotinylated fluorescent DNA probes bound with said beads to specific target DNA sequences on human chromosomes in an intact interphase cell from human biological samples; and f) generating the multiplex profiling of chromosomes in the intact interphase cell from the human biological samples including an individual profile for each of said chromosomes by reading, using one or more filter sets, said one to four different fluorescent signals emitted at said specific target DNA sequences on said human chromosomes in said intact interphase cell.

* * * * *